(12) United States Patent
Veit et al.

(10) Patent No.: US 7,713,229 B2
(45) Date of Patent: May 11, 2010

(54) DRUG DELIVERY PEN WITH EVENT NOTIFICATION MEANS

(75) Inventors: Eric D. Veit, Pleasanton, CA (US);
Adam Bylund, Jacksonville, OR (US);
Barry Weber, Livermore, CA (US);
Peter Luther, Pleasanton, CA (US);
Joseph McCluskey, Sharon, MA (US);
Jean Bidegainberry, San Francisco, CA (US)

(73) Assignee: Lifescan, Inc., Milpitas, CA (US)

( * ) Notice: Subject to any disclaimer, the term of this patent is extended or adjusted under 35 U.S.C. 154(b) by 72 days.

(21) Appl. No.: 10/981,830

(22) Filed: Nov. 5, 2004

(65) Prior Publication Data
US 2005/0182358 A1 Aug. 18, 2005

Related U.S. Application Data

(60) Provisional application No. 60/518,571, filed on Nov. 6, 2003.

(51) Int. Cl.
*A61M 5/30* (2006.01)

(52) U.S. Cl. ....................................................... 604/65

(58) Field of Classification Search .............. 604/93.01, 604/187, 207, 20, 891.1; 128/903
See application file for complete search history.

(56) References Cited

U.S. PATENT DOCUMENTS

| | | | |
|---|---|---|---|
| 3,837,339 A | 9/1974 | Aisenberg et al. |
| 3,923,426 A | 12/1975 | Theeuwes |
| 4,146,029 A | 3/1979 | Ellinwood, Jr. |
| 4,270,532 A | 6/1981 | Franetzki et al. |
| 4,282,872 A | 8/1981 | Franetzki et al. |
| 4,360,019 A | 11/1982 | Portner et al. |
| 4,373,527 A | 2/1983 | Fischell |
| 4,395,259 A | 7/1983 | Prestele et al. |
| 4,447,224 A | 5/1984 | DeCant, Jr. et al. |
| 4,475,901 A | 10/1984 | Kraegen et al. |
| 4,494,950 A | 1/1985 | Fischell |
| 4,515,584 A | 5/1985 | Abe et al. |
| 4,529,401 A | 7/1985 | Leslie et al. |
| 4,559,037 A | 12/1985 | Franetzki et al. |
| 4,562,751 A | 1/1986 | Nason et al. |
| 4,601,707 A | 7/1986 | Albisser et al. |
| 4,619,653 A | 10/1986 | Fischell |

(Continued)

FOREIGN PATENT DOCUMENTS

EP 0 098 592 1/1984

(Continued)

OTHER PUBLICATIONS

PCT Search Report mailed on Aug. 23, 2005.

(Continued)

*Primary Examiner*—Nicholas D Lucchesi
*Assistant Examiner*—Christopher D Koharski

(57) ABSTRACT

Devices, systems and methods are provided for drug delivery and the monitoring thereof. The systems include a drug delivery device, a holder for the drug delivery device when the device is not in use, a detector for detecting the presence of the drug delivery device within or close to the holder, and at least one algorithm for querying and prompting a user of the drug delivery device, wherein the at least one algorithm is activated upon removal of the drug delivery device from the holder.

22 Claims, 4 Drawing Sheets

U.S. PATENT DOCUMENTS

| | | | |
|---|---|---|---|
| 4,633,878 A | 1/1987 | Bombardieri |
| 4,636,144 A | 1/1987 | Abe et al. |
| 4,678,903 A | 7/1987 | Wlodarczyk et al. |
| 4,692,147 A | 9/1987 | Duggan |
| 4,714,462 A | 12/1987 | DiDomenico |
| 4,731,051 A | 3/1988 | Fischell |
| 4,731,726 A | 3/1988 | Allen |
| 4,734,360 A | 3/1988 | Phillips |
| 4,776,842 A | 10/1988 | Franetzki |
| 4,803,625 A | 2/1989 | Fu et al. |
| 4,810,243 A | 3/1989 | Howson |
| 4,826,810 A | 5/1989 | Aoki |
| 4,871,351 A | 10/1989 | Feingold |
| 4,900,666 A | 2/1990 | Phillips |
| 4,935,346 A | 6/1990 | Phillips et al. |
| 4,950,246 A | 8/1990 | Muller |
| 4,985,015 A | 1/1991 | Obermann et al. |
| 4,995,402 A | 2/1991 | Smith et al. |
| 5,019,974 A | 5/1991 | Beckers |
| 5,059,394 A | 10/1991 | Phillips et al. |
| 5,097,122 A | 3/1992 | Colman et al. |
| 5,135,479 A | 8/1992 | Sibalis et al. |
| 5,176,632 A | 1/1993 | Bernardi |
| 5,204,670 A | 4/1993 | Stinton |
| 5,216,597 A | 6/1993 | Beckers |
| 5,251,126 A | 10/1993 | Kahn et al. |
| 5,304,468 A | 4/1994 | Phillips et al. |
| 5,306,623 A | 4/1994 | Kiser et al. |
| 5,364,838 A | 11/1994 | Rubsamen |
| 5,368,562 A | 11/1994 | Blomquist et al. |
| 5,376,070 A | 12/1994 | Purvis et al. |
| 5,417,222 A | 5/1995 | Dempsey et al. |
| 5,418,142 A | 5/1995 | Kiser et al. |
| 5,426,032 A | 6/1995 | Phillips et al. |
| 5,433,736 A | 7/1995 | Nilsson |
| 5,497,772 A | 3/1996 | Schulman et al. |
| 5,507,288 A | 4/1996 | Bocker et al. |
| 5,515,170 A | 5/1996 | Matzinger et al. |
| 5,526,120 A | 6/1996 | Jina et al. |
| 5,536,249 A | 7/1996 | Castellano et al. |
| 5,544,651 A | 8/1996 | Wilk |
| 5,544,661 A | 8/1996 | Davis et al. |
| 5,558,638 A | 9/1996 | Evers et al. |
| 5,558,640 A | 9/1996 | Pfeiler et al. |
| 5,563,042 A | 10/1996 | Phillips et al. |
| 5,569,186 A | 10/1996 | Lord et al. |
| 5,569,187 A | 10/1996 | Kaiser |
| 5,593,390 A | 1/1997 | Castellano et al. |
| 5,620,863 A | 4/1997 | Tomasco et al. |
| 5,658,250 A | 8/1997 | Blomquist et al. |
| 5,665,065 A | 9/1997 | Colman et al. |
| 5,678,562 A | 10/1997 | Sellers |
| 5,708,247 A | 1/1998 | McAleer et al. |
| 5,728,074 A | 3/1998 | Castellano et al. |
| 5,735,887 A | 4/1998 | Barreras, Sr. et al. |
| 5,753,452 A | 5/1998 | Smith |
| 5,764,159 A | 6/1998 | Neftel |
| 5,773,452 A | 6/1998 | Sauerberg et al. |
| 5,780,304 A | 7/1998 | Matzinger et al. |
| 5,789,255 A | 8/1998 | Yu |
| 5,807,336 A | 9/1998 | Russo et al. |
| 5,820,602 A | 10/1998 | Kovelman et al. |
| 5,840,020 A | 11/1998 | Heinonen et al. |
| 5,843,691 A | 12/1998 | Douglas et al. |
| 5,846,486 A | 12/1998 | Pugh |
| 5,885,245 A | 3/1999 | Lynch et al. |
| 5,895,371 A | 4/1999 | Levitas et al. |
| 5,897,493 A | 4/1999 | Brown |
| 5,899,931 A | 5/1999 | Deschamp et al. |
| 5,925,021 A | 7/1999 | Castellano et al. |
| 5,928,195 A | 7/1999 | Malamud et al. |
| 5,935,099 A | 8/1999 | Peterson et al. |
| 5,950,632 A | 9/1999 | Reber et al. |
| 5,951,836 A | 9/1999 | McAleer et al. |
| 5,968,836 A | 10/1999 | Matzinger et al. |
| 5,972,294 A | 10/1999 | Smith et al. |
| 6,024,539 A | 2/2000 | Blomquist |
| 6,024,699 A | 2/2000 | Surwit et al. |
| 6,038,676 A | 3/2000 | Yanes et al. |
| 6,134,504 A | 10/2000 | Douglas et al. |
| 6,144,922 A | 11/2000 | Douglas et al. |
| 6,192,891 B1 * | 2/2001 | Gravel et al. ............... 604/187 |
| 6,193,873 B1 | 2/2001 | Ohara et al. |
| 6,238,338 B1 | 5/2001 | DeLuca et al. |
| 6,241,704 B1 | 6/2001 | Peterson et al. |
| 6,241,862 B1 | 6/2001 | McAleer et al. |
| 6,248,093 B1 | 6/2001 | Moberg |
| 6,270,455 B1 * | 8/2001 | Brown ......................... 600/300 |
| 6,277,098 B1 | 8/2001 | Klitmose et al. |
| 6,283,944 B1 | 9/2001 | McMullen et al. |
| 6,284,125 B1 | 9/2001 | Hodges et al. |
| 6,336,900 B1 | 1/2002 | Alleckson et al. |
| 6,378,702 B1 | 4/2002 | Hintzig |
| 6,406,605 B1 | 6/2002 | Moles |
| 6,418,346 B1 | 7/2002 | Nelson et al. |
| 6,443,890 B1 | 9/2002 | Schulze et al. |
| 6,444,115 B1 | 9/2002 | Hodges et al. |
| 6,475,372 B1 | 11/2002 | Ohara et al. |
| 6,482,185 B1 | 11/2002 | Hartmann |
| 6,514,230 B1 * | 2/2003 | Munk et al. ................. 604/207 |
| 6,529,446 B1 | 3/2003 | de la Huerga |
| 6,540,672 B1 * | 4/2003 | Simonsen et al. ........... 600/300 |
| 6,554,798 B1 * | 4/2003 | Mann et al. ................. 604/131 |
| 6,585,698 B1 | 7/2003 | Packman et al. |
| 6,595,956 B1 | 7/2003 | Gross et al. |
| 6,641,533 B2 | 11/2003 | Causey, III et al. |
| 6,656,114 B1 | 12/2003 | Poulsen et al. |
| 6,669,663 B1 | 12/2003 | Thompson |
| 6,681,003 B2 | 1/2004 | Linder et al. |
| 6,723,068 B2 | 4/2004 | Lavi et al. |
| 6,733,655 B1 | 5/2004 | Davies et al. |
| 6,781,522 B2 | 8/2004 | Sleva et al. |
| 6,790,178 B1 | 9/2004 | Mault et al. |
| 6,817,986 B2 * | 11/2004 | Slate et al. ..................... 604/68 |
| 6,837,876 B2 | 1/2005 | Bally et al. |
| 6,869,413 B2 | 3/2005 | Langley et al. |
| 6,939,324 B2 | 9/2005 | Gonnelli et al. |
| 6,942,646 B2 | 9/2005 | Langley et al. |
| 6,951,631 B1 | 10/2005 | Catt et al. |
| 7,133,329 B2 | 11/2006 | Skyggebjerg et al. |
| 7,220,244 B2 | 5/2007 | Kriesel |
| 7,282,029 B1 | 10/2007 | Poulsen et al. |
| 7,397,730 B2 | 7/2008 | Skyggebjerg et al. |
| 7,534,230 B2 | 5/2009 | Follman et al. |
| 2003/0058110 A1 | 3/2003 | Rich |
| 2003/0099158 A1 | 5/2003 | De la Huerga |
| 2003/0109827 A1 | 6/2003 | Lavi et al. |
| 2003/0114885 A1 * | 6/2003 | Nova et al. ..................... 607/2 |
| 2003/0220814 A1 | 11/2003 | Gordon |
| 2004/0023972 A1 | 2/2004 | Sundermann et al. |
| 2004/0039255 A1 | 2/2004 | Simonsen et al. |
| 2004/0122355 A1 | 6/2004 | Langley et al. |
| 2004/0171983 A1 | 9/2004 | Sparks et al. |
| 2005/0049179 A1 | 3/2005 | Davidson et al. |
| 2005/0065472 A1 | 3/2005 | Cindrich et al. |
| 2005/0119524 A1 | 6/2005 | Sekine et al. |
| 2005/0119618 A1 | 6/2005 | Gonnelli et al. |
| 2005/0171512 A1 | 8/2005 | Flaherty et al. |
| 2005/0182358 A1 | 8/2005 | Veit et al. |
| 2005/0197553 A1 | 9/2005 | Cooper |
| 2005/0197621 A1 | 9/2005 | Poulsen et al. |
| 2006/0010098 A1 | 1/2006 | Goodnow et al. |
| 2006/0074381 A1 | 4/2006 | Malave et al. |
| 2006/0122577 A1 | 6/2006 | Poulsen et al. |

| | | | |
|---|---|---|---|
| 2006/0189939 A1 | 8/2006 | Gonnelli et al. | |
| 2006/0264894 A1 | 11/2006 | Moberg et al. | |
| 2007/0016449 A1 | 1/2007 | Cohen et al. | |
| 2007/0123819 A1 | 5/2007 | Mernoe et al. | |
| 2007/0123829 A1 | 5/2007 | Atterbury et al. | |
| 2007/0219496 A1 | 9/2007 | Kamen et al. | |
| 2007/0239486 A1 | 10/2007 | Gordon et al. | |
| 2007/0244469 A1 | 10/2007 | Ozeri et al. | |
| 2007/0299401 A1 | 12/2007 | Alferness et al. | |
| 2008/0097318 A1 | 4/2008 | Adams | |
| 2008/0097324 A1 | 4/2008 | Adams et al. | |
| 2008/0119790 A1 | 5/2008 | Hawkins et al. | |

FOREIGN PATENT DOCUMENTS

| | | | |
|---|---|---|---|
| EP | 0 300 552 | | 1/1989 |
| EP | 0320749 B1 | | 9/1996 |
| EP | 0 880 936 | | 12/1998 |
| EP | 1110569 | * | 12/2000 |
| EP | 0483595 B1 | | 12/2001 |
| EP | 02388054.5 | | 11/2002 |
| EP | 0949505 B1 | | 3/2006 |
| GB | 2 129 203 | | 5/1984 |
| GB | 2443434 | | 5/2008 |
| WO | WO 95/24233 | | 9/1995 |
| WO | WO 97/00708 | | 1/1997 |
| WO | 97008605 | | 3/1997 |
| WO | WO 99/43283 A1 | | 9/1999 |
| WO | WO 00/18449 | | 4/2000 |
| WO | WO 00/32258 | | 6/2000 |
| WO | WO 00/45696 | | 8/2000 |
| WO | WO 00/78210 | | 12/2000 |
| WO | WO 01/73109 | | 10/2001 |
| WO | WO 01/73124 | | 10/2001 |
| WO | WO 02/06806 | | 1/2002 |
| WO | WO 02/49507 | | 6/2002 |
| WO | WO 2002/062212 | | 8/2002 |
| WO | WO 02/094440 | | 11/2002 |
| WO | WO 03/047426 A1 | | 6/2003 |
| WO | WO 2004/010231 | | 1/2004 |
| WO | 2005/046559 | | 5/2005 |
| WO | 2005/093629 | | 10/2005 |
| WO | 2006/037802 | | 4/2006 |
| WO | 2007/115039 | | 10/2007 |
| WO | 2008/060827 | | 5/2008 |
| WO | 2008/106070 | | 9/2008 |

OTHER PUBLICATIONS

K. Irsigler, et al., "Long-term Continuous Intraperitoneal Insulin Infusion with an Implanted Remote-Controlled Insulin Infusion Device," Diabetes, vol. 30, 1981, pp. 1072-1075.

G.A. Carlson, et al., "An Implantable, Remotely Programmable Insulin Infusion System," Medical Progress Through Technology, 9, 1982, pp. 17-25.

M. Franetzki, et. al., "Insulin Delivery Devices: What Has Been Achieved, What Is Feasible, and Which Medical Research Is Still Needed to Specify and Optimize Future Devices?," Artificial Systems for Insulin Delivery, 1983, pp. 107-113.

Robert E. Fischell, "Microcomputer-Controlled Devices for Human Implantation," Johns Hopkins API Technical Digest, vol. 4, No. 2, 1983, pp. 96-103.

R.E. Fishell, et al., "A Programmable Implantable Medication System: Application to Diabetes," Proceedings of the Sixteenth Annual Hawaii International Conference on System Sciences, 1983, pp. 229-234.

Manfred Franetzki, "Drug Delivery by Program or Sensor Controlled Infusion Devices," Pharmaceutical Research, 1984, pp. 237-244.

Albisser, et al., "Intelligent Instrumentation in Diabetic Management," Critical Reviews in Biomedical Engineering, 1989, vol. 17, Issue 1, pp. 1-24.

Fabietti, et al., "Wearable System for Acquisition, Processing and Storage of the Signal from Amperometric Glucose Sensors," The International Journal of Artificial Organs, vol. 14, No. 3, 1991, pp. 175-178.

Robert E. Fischell, "The Development of Implantable Medical Devices at the Applied Physics Laboratory," Johns Hopkins APL Technical Digest, vol. 13, No. 1, 1992, pp. 233-243.

Cress, et al., "Portable Data Acquisition and Control Apparatus for Implanted Drug Infusion Pump Interrogation," ASAIO Journal, 1993, pp. M695-M698.

Black, et al., "Integrated Sensor-Telemetry System for In Vivo Glucose Monitoring," Sensors and Actuators B 31, 1996, pp. 147-153.

Atanasov, et al., "Short-term Canine Implantation of a Glucose Monitoring-Telemetry Device," Med. Eng. Phys, vol. 18, No. 8, 1996, pp. 632-640.

Belardinelli, et al., "Advanced Technology for Personal Biomedical Signal Logging and Monitoring," Proceedings of the $20^{th}$ Annual International Conference of the IEEE Engineering in Medicine and Biology Society, vol. 20, No. 3, 1998, pp. 1295-1298.

Beach, et al., "Subminiature Implantable Potentiostat and Modified Commercial Telemetry Device for Remote Glucose Monitoring," IEEE Transactions on Instrumentation and Measurement, vol. 48, No. 6, Dec. 1999, pp. 1239-1245.

Jaremko, et al., "Advances Toward the Implantable Artificial Pancreas for Treatment of Diabetes," Diabetes Care, vol. 21, No. 3, Mar. 1998, pp. 444-450.

Klein, et al., "A Sophisticated Programmable Miniaturised Pump for Insulin Delivery," Med. Progr. Technol. 7, 1980, pp. 193-197.

Prestele, et al., "State of Development of Program-Controlled Implantable Insulin Delivery Systems," Artificial Systems for Insulin Delivery, 1983, pp. 141-153.

Prestele, et al., "Development of Program-controlled Portable Insulin Delivery Devices," Diabetes Care, vol. 3, No. 2, Mar.-Apr. 1980, pp. 362-367.

Saudek, et al., "The Programmable Implantable Medication System (PIMS): Design Features and Pre-Clinical Trails," Horm. meta. Res. 22, 1990, pp. 201-206.

Christopher D. Saudek, MD, "Future Developments in Insulin Delivery Systems," Diabetes Care, vol. 16, Supplement 3, Dec. 1993, pp. 122-132.

Schade, et al., "Future Therapy of the Insulin-dependent Diabetic Patient—The Implantable Insulin Delivery System," Diabetes Care, vol. 4, No. 2, Mar.-Apr. 1981, pp. 319-324.

Albisser, et al., "Insulin Dosage Adjustment Using Manual Methods and Computer Algorithms: A Comparative Study," Med. & Biol. Eng. & Comput., 1986, 24, pp. 577-584.

Parker, et al., "Model Predictive Control for Infusion Pump Insulin Delivery," $18^{th}$ Annual International Conference of the IEEE Engineering in Medicine and Biology Society, Amsterdam, 1996, 6.3.4: Physiological Modelling—Glucose, pp. 1822-1823.

M. Franetzki, et al., "Design and Data of a Compact Device for Sustained Program-Controlled Medicament Infusion" Hormone and Metabolic Research, Supplement Series (1982), 12 (Islet-Pancreas-Transplant. Artif. Pancreas), 169-172, ISSN: 0170-5903, ISBN: 086577062x.

Lord, et al., "MiniMed Technologies Programmable Implantable Infusion Systyem," Annals of the New York Academy of Sciences, 1988;531:66-71.

Prestele, et al., "A Remote-Programmable Implantable Insulin Dosing Device Part 1" Techincal Concept and Features, Hormone and Metabolic Research, Supplement Series (1982), 12 (Islet-Pancreas-Transplant. Artif. Pancreas), 304-7, ISSN: 0170-5903, ISBN: 086577062x.

Christopher D. Saudek, "Development of Implantable Insulin Infusion Devices", Methods in Diabetes Research, vol. II: Clinical Methods, 1986, pp. 347-360, Editors Clarke, William; Larner, Joseph; et al.

* cited by examiner

DRUG DELIVERY PEN WITH EVENT NOTIFICATION MEANS

CROSS-REFERENCE TO RELATED APPLICATIONS

This application claims the benefit of U.S. Provisional patent application Ser. No. 60/518,571, filed on Nov. 6, 2003, the disclosure of which is incorporated herein by reference in its entirety.

FIELD OF THE INVENTION

The present invention generally relates to a user-based drug delivery system. More particularly, the invention relates to a drug delivery system that includes a drug delivery instrument or pen provided in a container or case in which the presence or proximity of the pen to the case is detected by means configured within the case or one or more other components of the system, such as a meter, or Personal Digital Assistant (PDA) contained therein.

BACKGROUND OF THE INVENTION

Medication infusion devices and physiological fluid characteristic monitoring devices are known in the medical field. One very common application of such devices is the delivery of insulin to and the monitoring of blood glucose levels of diabetics. Increased portability and ease of use of such devices have enabled the diabetic to administer a self-regulated medical treatment regime which in turn provides an increased level of patient autonomy and privacy. This is particularly beneficial since a diabetic's glucose levels may vary daily or hourly.

Such self-regulated diabetic treatment regimes often include the self-administration, either by injection and/or ingestion, of various medications, e.g., insulin. In addition to a high degree of medication compliance, for such self-regulated regimes to work effectively and safely, the patient needs to closely monitor the times at which medication is taken and may need to record or document corresponding medically relevant self-monitoring information, e.g., blood glucose level, insulin dosage, etc. The monitoring of such data helps to determine the current status and course of action (regime change) of future actions. Because the recordation or awareness of this information can be time consuming and inconvenient, particularly if done with a paper logbook, it is desirable that recordation, compilation and tracking of this type of information be as seamless and time-efficient to the user as possible.

Accordingly, there is continued interest in the development of new devices and methods for the patient-regulated monitoring and recordation of medical information, including but not limited to drug administration (injection) time and dosage, analyte concentration, e.g., glucose levels, etc. Of particular interest would be the development of a patient-controlled medication administration and monitory system which provides the patient with flexibility and control, increases convenience, privacy and ease of use for the patient, and enhances portability of system components (e.g., glucose measurement meter, insulin injector, test strips, needles, lancets, etc.).

SUMMARY OF THE INVENTION

Devices, systems and methods are provided for drug delivery and the monitoring thereof. Generally, a system of the present invention includes a drug delivery device, a holder for the drug delivery device when the device is not in use, a detector for detecting the presence of the drug delivery device within or close to the holder, and at least one algorithm for querying and prompting a user of the drug delivery device, wherein the at least one algorithm is activated upon removal of the drug delivery device from the holder. The detector may be a mechanical switch, a magnetic switch, a density switch, a capacitive switch, an electrical sensor, or an optical sensor. The holder, the detector and the at least one algorithm are incorporated into a case for housing the system. The system may further include an analyte measurement meter where the at least one algorithm is stored in the analyte measurement meter, whereby the meter is caused to turn on upon removal of the drug delivery device from the holder. In certain embodiments, the system includes means for communicating with a device for storing user information, such as drug dosing information.

A particular application of the invention is an insulin injection system which includes a meter adapted for the measurement of glucose concentration in a blood sample, an insulin injector, and a storage space for the insulin injector, the storage space including a detector adapted to activate an algorithm in the meter when the insulin injector is removed from or placed in the storage space. A case is provided which is configured for housing the meter and defining the storage space. In certain embodiments, the system includes wireless communication means for transmitting and receiving data to and from an external device, such as a cell phone, a PDA, a computer, etc.

The present invention also provides methods of monitoring the use of a drug delivery device, such as an insulin injector, where the methods generally include storing the drug delivery device when the device is not in use, removing the drug delivery device from storage, detecting the removal of the drug delivery device from storage, and activating an algorithm wherein the user of the drug delivery device is queried for information regarding use of the drug delivery device, such as drug dosage information. Other data, such as the time at which the drug delivery device is removed from storage, may be automatically recorded and stored in memory. In certain variations, the method includes transmitting the information to a data storage device.

An advantage of the present invention is the automation of the task of logging drug delivery and monitoring data, which eases the burden on the self-administering user from the effort and time of logging such information, and from remembering to do so.

These and other objects, advantages, and features of the invention will become apparent to those persons skilled in the art upon reading the details of the methods and systems of the present invention which are more fully described below.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

Before the present invention is described, it is to be understood that this invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. Thus, for example, reference to "a test strip" includes a plurality of such test strips and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided might be different from the actual publication dates which may need to be independently confirmed.

While the invention is primarily described in diabetic applications, in particular in the context of insulin delivery and glucose concentration measurements, it is understood that the present invention is not so limited and may be employed in any drug delivery application, particularly where the drug delivery regime is self-administered. Other applications include, for example, the administration of humane growth hormones, asthma medication, blood thinners.

Figure 1:
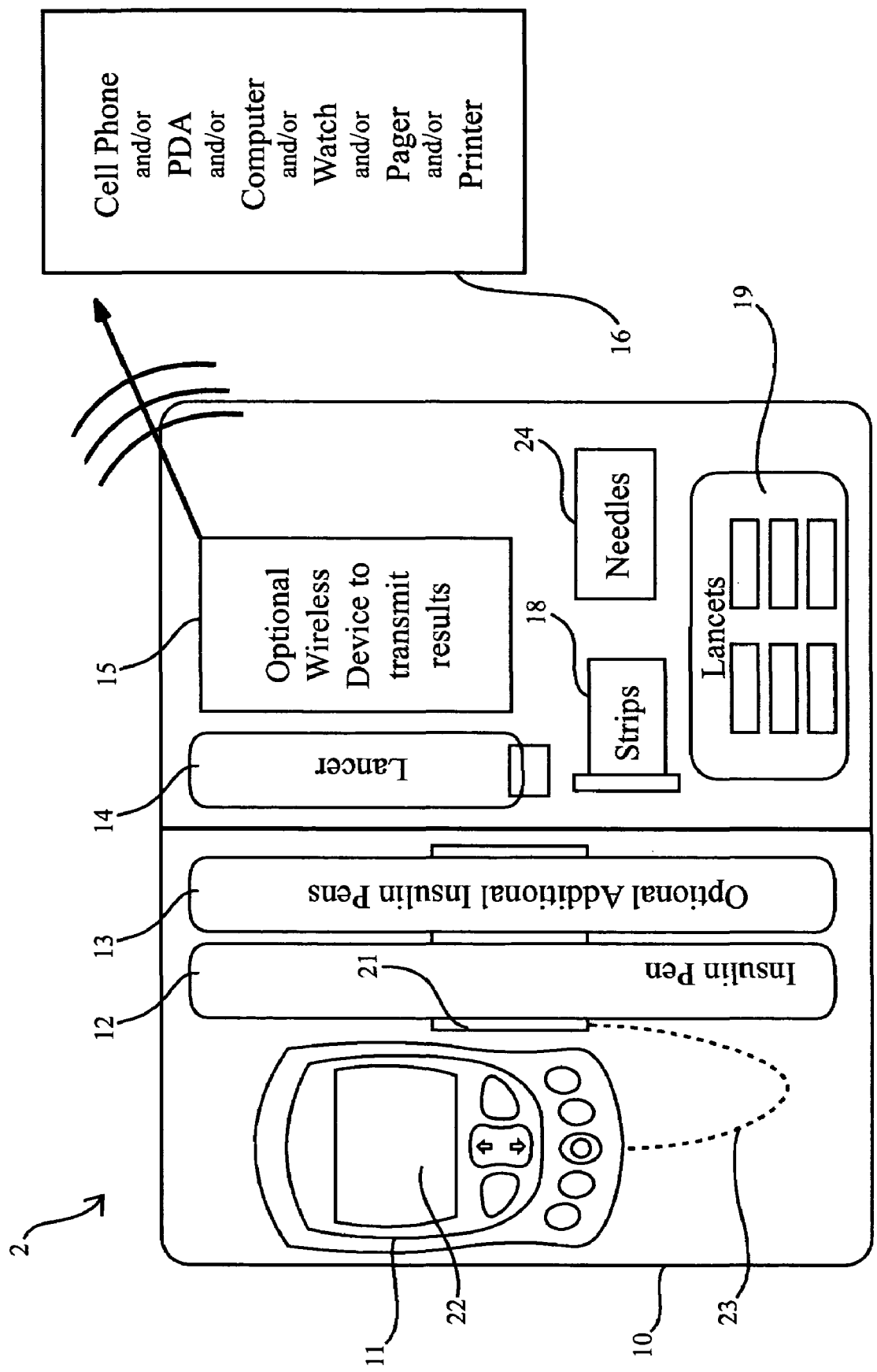
FIG. 1 is a schematic illustration of an exemplary embodiment of a system according to the present invention.

Referring now to the drawings, FIG. 1 illustrates of a schematic representation of a system 2 of the present invention which includes a storage/carry case or container 10 which provides various devices and components for use by a patient for the self-monitoring of glucose levels and the self-administration of insulin. In particular, the system includes a glucose measurement meter 11 and one or more drug delivery devices 12 and 13, such as insulin injector pens or insulin syringes. Meter 11 may be any meter of the appropriate size with functionality as described herein. The delivery devices may be of the same or of a different type. One skilled in the art will recognize that any number of drug delivery devices may be included in case 10.

Case 10 may be formed from soft, pliable materials including leather, vinyl, plastic, or other suitable material known to those skilled in the art. Alternatively, case 10 may be made of a rigid material such as injection molded plastic. Closure of case 10 may be accomplished with a zipper, snap, catch, latch or any suitable securing means. Meter 11 may be secured in case 10 by a hook and loop fastener (e.g., Velcro), a loop, adhesive, or any other suitable means such that meter 11 is easily removable from case 10 by the user. Case 10 may have a configuration to attach to other modular or auxiliary cases which contain the same or similar devices and supplies. Such an auxiliary case may be helpful when traveling to ensure the availability of supplies and medication to treat oneself at any time.

Optionally, case 10 may further include compartments or containers for holding a variety of devices and components for accessing or collecting samples of blood or body fluid, such as a lancing mechanism 14, lancets 19 and needles 24. Case 10 may further include devices, such as test strips 18, for transferring and presenting the accessed or collected samples of blood or body fluid to within meter 11.

Case 10 is configured to provide communication between certain components contained within case 10. For example, case 10 may include a detection means 21 for detecting the presence or removal of drug delivery device 12 and/or 13 within or from case 10. Detection device 21 may be a switch or sensor, such as a mechanical, magnetic, density, capacitive switch, or an electrical or optical sensor, such as an infrared sensor.

Detection device 21 may be configured as shown or embedded within a cradle, cavity or holder which provides a secure means, such as a snap-fit configuration, for retaining the drug delivery devices within case 10. For example, an infrared emitter and detector may be separately mounted on opposing sides of the pen cradle. If the injector pen is present within the cradle, the infrared beam emitted by the emitter will be blocked from receipt by the infrared detector. Where the pen is absent from the cradle, the infrared beam is detected by the detector and a signal is sent to case 10 or meter 11 indicating such.

Figure 2:
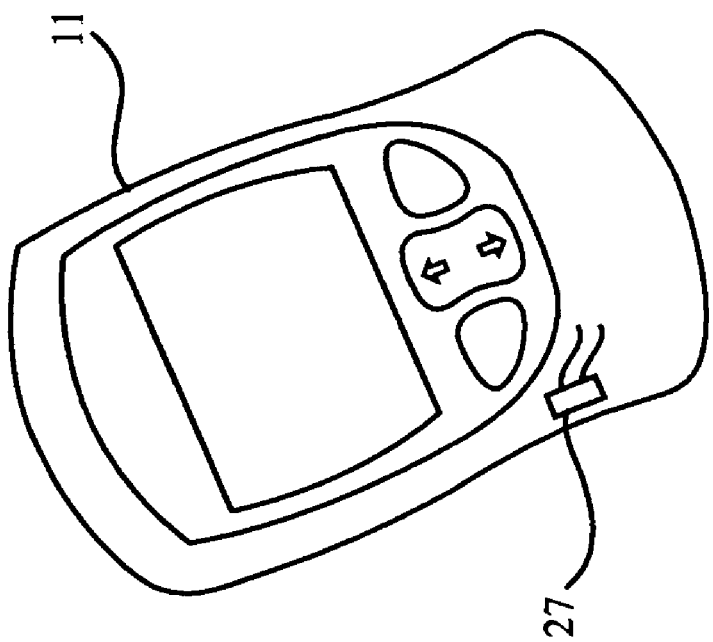
FIG. 2 is a perspective view of another exemplary embodiment of a system according to the present invention.
Figure 2:
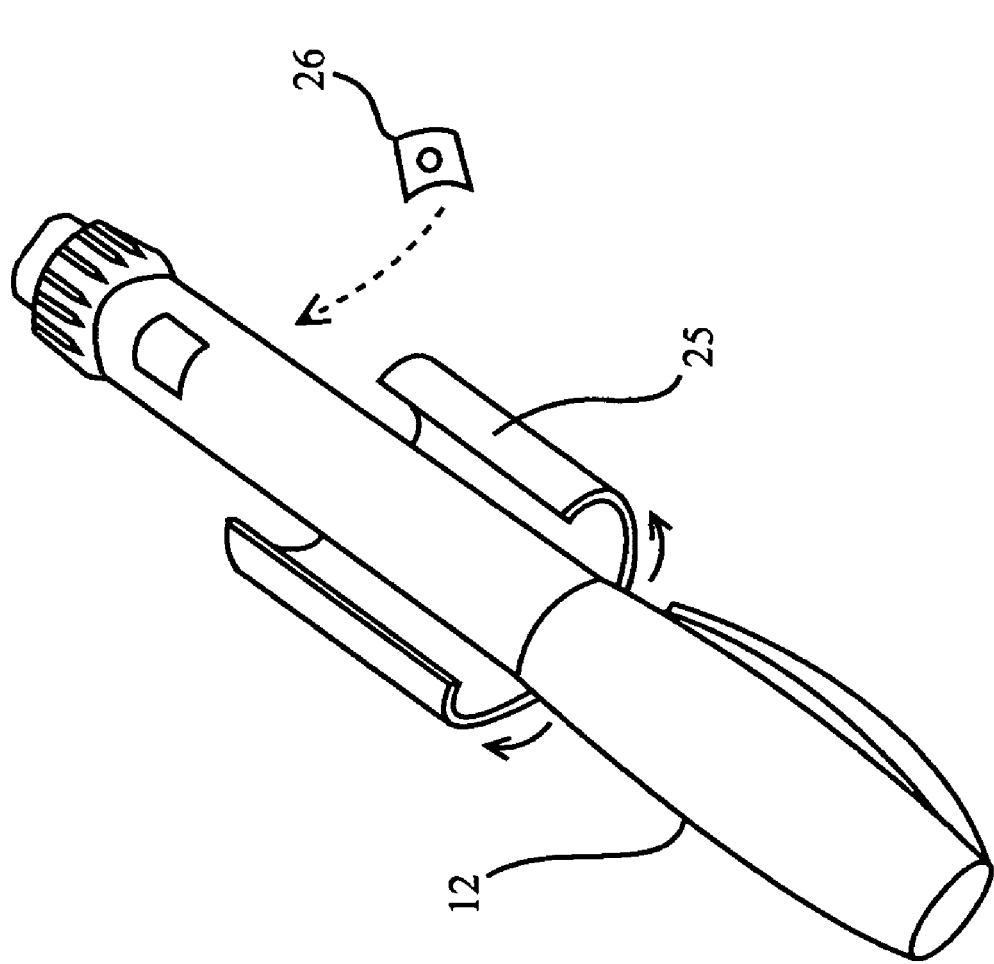

Alternatively, as illustrated in FIG. 2, the detection means may be configured for detecting the proximity of device 12 and/or 13 to case 10 or meter 11. For example, the detection means may include proximity labels 25 or 26 which may be removably affixed or adhered to drug delivery device 12 and a corresponding proximity label 27 which is provided on meter 11. The proximity labels may be in the form of a magnetic label with adhesive backing or other sensor type which bay be attached to drug delivery pen 12. Meter 11 has corresponding electronics which detect the position insulin pen 12 with respect to meter 11. Therefore movement of insulin pen 12 can be detected and monitored with meter 11. For example, when the injection device is moved a specified distance, e.g., 6 inches or more, from meter 11, meter 11 would be trigger on. It is an advantage of this embodiment in that drug delivery pen 12 does not have to be attached to case 10 while at the same time the initiation of use for drug delivery pen 12 can still be monitored.

Still yet the drug delivery device detection means may include a radio frequency (RF) generating means incorporated within the drug delivery pen 10 or under a cap provided on the pen such that, when the cap is removed from the pen, an RF signal is transmitted to case 10 or meter 11 which has an RF receiver means. This action is recorded and can be interacted (graphed) with the self-monitoring information. This embodiment reduces the active steps required to be performed by the patient, and as such, eases compliance to the prescribed treatment plan.

With any configuration of the detection means 21, the switch or sensor may be communicatively coupled to meter 11 and/or to a microprocessor and memory chip or the like which is built in to the case itself, where meter 11 and the microprocessor/memory chip are also electrically coupled, such as by way of a serial communication port or electrical connection 23. Alternatively, meter 11 may be integrated into case 10 where, collectively, the two form a PDA device.

Where the drug injector is preloaded with the drug to be delivered, another sensor may be employed to automatically determine the amount of drug dispensed from the injector. In this way, the patient is relieved from logging or recording this information.

Case 10 may be further equipped with a meter detector (not shown) to detect the presence and removal of meter 11 from case 10, and as such, in order to determine whether the patient has performed a glucose measurement test prior to an insulin dosing. In this way, the appropriate prompts and queries can be made to the user. Such a meter detector may be a mechanical single pole switch mounted within the portion of case 10 in which meter 11 is retained.

Case 10 may further include a sensor (not shown) for detecting whether the case cover is open or closed. A suitable sensor may be employ two flexible magnetic tape strips placed on opposite side of the case cover. When the case is closed, the system may be triggered to go into a "sleep" mode to save battery power.

Case 10 may further include means for enabling the communication between the case, meter and/or PDA and a device or system 16 external to case 10. Examples of such external devices 16 include a cell phone, PDA, computer, watch, pager, printer, or any other device capable of receiving and/or transmitting wireless communication. To effect such, a wireless communication device 15 is integrated within the case to transmit data to and possibly receive data from these external devices 16. Furthermore, wireless communication device 15 may be capable of exchanging data with meter 11 and/or drug delivery devices 12, 13. Wireless communication device 15 may transmit information through, for example, an RF signal (e.g., Bluetooth link).

Figure 3:
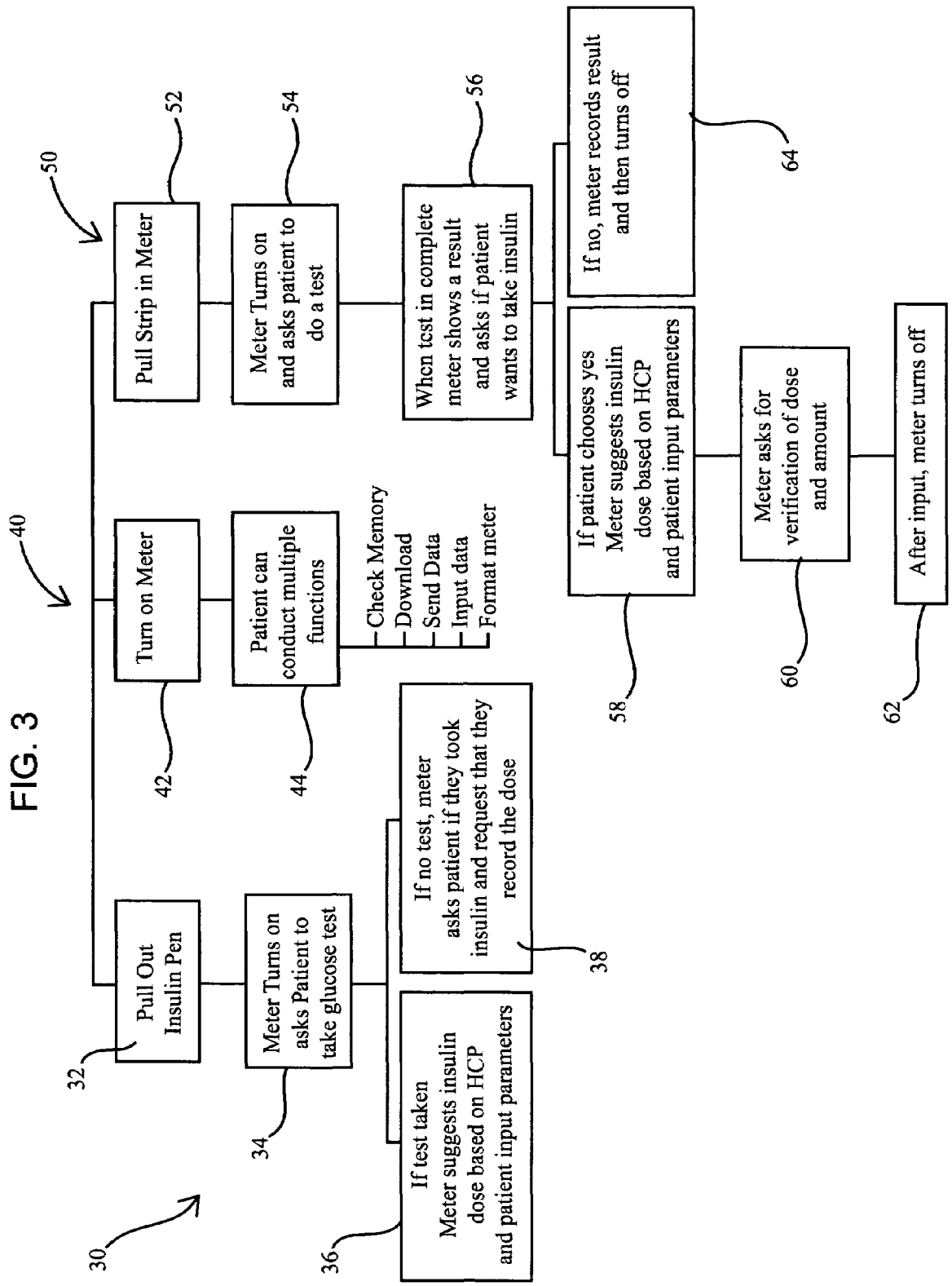
FIG. 3 is a flowchart illustrating a sequence of steps in a process according to one or more exemplary embodiments of the method of the present invention.

In use, system 2 may be configured to operate according to any one or more of the protocols provided in the block diagram of FIG. 3. With respect to protocol 30 of FIG. 3, when a drug delivery device 12, 13 is removed or is moved a specified distance (step 32), from case 10, the detector or sensor 21 sends or transmits a signal to meter 11 indicating that the drug delivery device has been removed and, preferably, crating a time stamp record of the event. This in turn triggers meter 11 to turn on and to display a visual (via a display 22) and/or provide audio (via a microphone, not shown) prompt or query to the user (step 34). For example, the user may be queried or prompted to conduct a glucose measurement test or to enter drug delivery information. If the user conducts a glucose measurement test with meter 11, meter 11 prompts the user with a suggested dosage of insulin to be administered based on an algorithm, input from the Health Care Practitioner (HCP) and/or other parameters previously or presently entered into the meter by the user (step 36). The user may or may not dose himself/herself with drug delivery device 12 with the suggested dosage. The user may opt to administer a dosage other than the suggested dosage where the real-time circumstances are such that dictate such. Such a situation may arise, for example, where there is a change in the anticipated or typical intake of carbohydrates by the diabetic, e.g., during a meal, a patient finds himself eating an amount of carbohydrates greater or less than what he or she anticipated prior to the meal. At other times, the user may not elect to conduct a glucose measurement but may nonetheless administer a dosage of insulin. This is a likely scenario where the patient's blood glucose levels are fairly predictable at any given time, e.g., after a meal. If no glucose measurement test is conducted, meter 11 will query the user as to whether a dosage of insulin was administered, and if so, requests the user to enter and verify the drug dosage information (step 38). To facilitate entry of the dosing information, the system may be configured to initially display a preset digital readout, for example, 1 unit of insulin and the user may adjust that unit value, preferably, by up-down toggle keys on meter 11 or on the PDA. Once entered, meter 11 stores the dosing data into meter's memory. The dosing data may then be automatically transmitted or prompted to be transmitted by the user to an external device 16 by wireless communication device 15. Upon placement of drug delivery device 12, 13 back into case 10, meter 11 may be triggered to turn off.

As provided in protocol flowchart 40 of FIG. 3, system 2 and meter 11 may be configured to be turned on and off by a user activated switch (step 42) and to allow the user to conduct multiple functions (step 44), such as check available system memory, download data, algorithms or programs, send and input data, and customize or format the meter or PDA. As provided in protocol flowchart 50, meter 11 can also be configured to turn on by insertion of a test strip 18 into meter 11 (step 52) which in turn triggers protocol steps (steps 54-64) similar to those provided by protocol flow chart 30.

Figure 4:
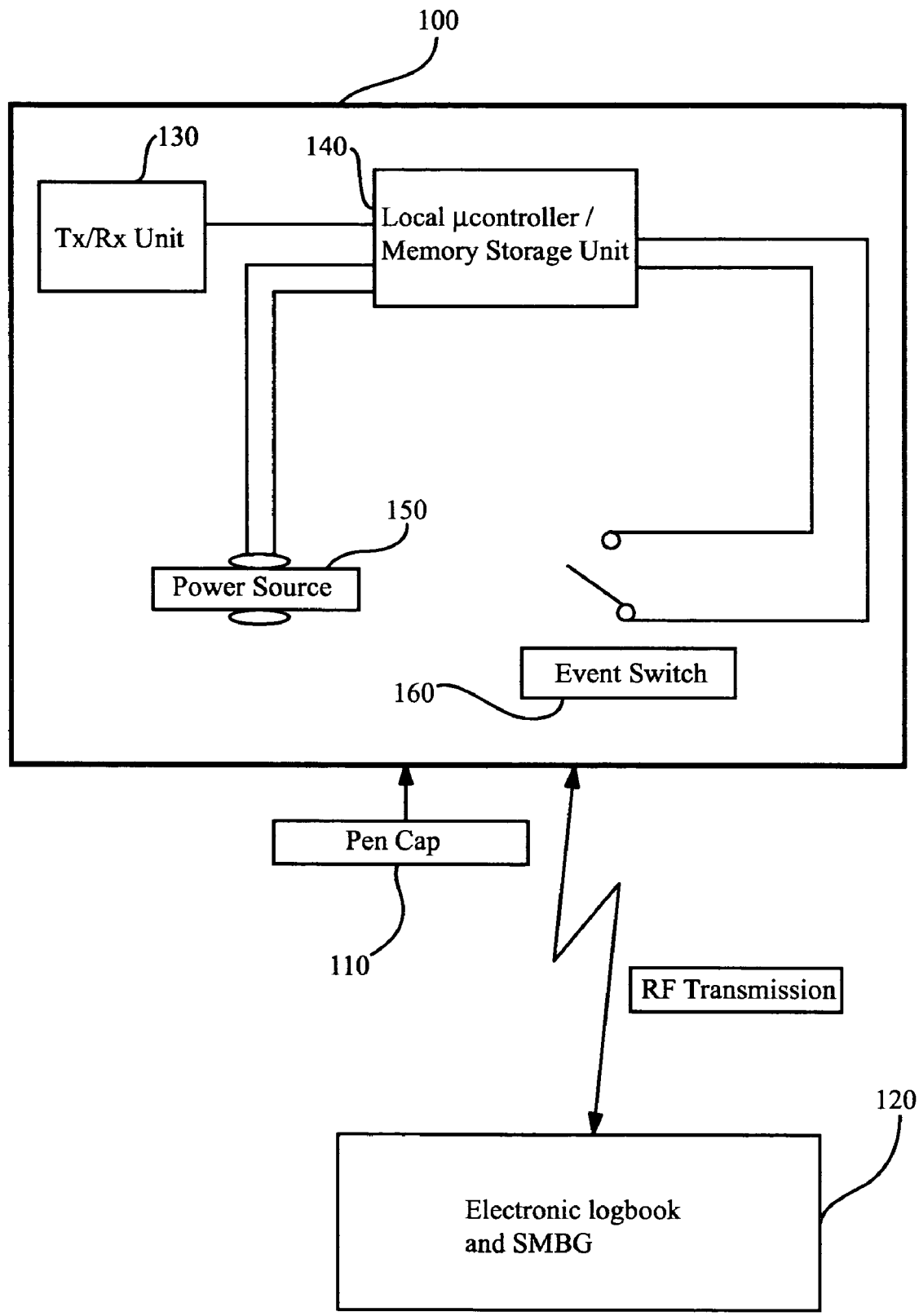
FIG. 4 is a schematic illustration of another exemplary embodiment of a system according to an embodiment of the present invention.

FIG. 4 is a schematic representation of a glucose monitoring system of the present invention which includes an insulin pen 100, a pen cap 110, and a glucose meter 120. Both insulin pen 100 and pen cap 110 have a housing which my be made of a durable IM plastic that is resistant to ware and tear as well as a variety of common household cleaning agents (bleach and alcohol) and personal use chemicals (hand moisturizers). Insulin pen 100 includes an RF transceiver unit (hereinafter referred to as RF Tx/Rx unit 130), local microcontroller 140, power source 150 and event switch 160. Insulin pen cap 110 is adapted to either press fit or thread fit with insulin pen 100. Insulin pen cap 110 is positioned such that event switch 160 is actuated when insulin pen cap 110 is removed from insulin pen 100. Local microcontroller 140 may also include a memory element. In addition local microcontroller may control the radio, timing, power management, event storage and local electronics (i.e., event switch 160). Event switch 160 may be a mechanical switch that closes a circuit when activated. This activation occurs when either insulin pen cap 110 is removed from insulin pen 100. During this activation, an RF signal may be sent from insulin pen 100 to glucose meter 120. The activation of switch 160 may be recorded and stored by local microcontroller 140. There are numerous examples known to one skilled in the art of switches that can be activated by user actions (i.e. pressure release). Power source 150 supplies power to RF Tx/Rx unit 130, local microcontroller 140 and event switch 160. Power source 150 is electrically coupled to the various components via contacts that may or may not be integrated into insulin pen cap 110.

RF Tx/Rx 130 may include transceiver, for example a Chipcon CC 1000 transceiver and a wire loop antenna which uses a frequency of 433 MHz FM band. An example of a suitable power supply 150 is a Silver Oxide RayOVac 357. A non-limiting example of event switch 160 may be Panasonic Pushbutton switch EVQ-PAC04M.

In an alternative embodiment which reduces electronic components of insulin pen 100, RF Tx/Rx unit 130 and local microcontroller 140 may be combined into a single package where the memory is used is an external EEPROM. Non-limiting examples which integrate RF Tx/Rx unit 130 and local microcontroller 140 include Texas Instrument Mixed Signal Processors (MSP) or Chipcon CC1010.

In another alternative embodiment which reduces power consumption by insulin pen 100, local microcontroller 140 and power source 150 may be replaced with a radio frequency identification tag (RFID). In order to communicate with the RFID, glucose meter 120 will need a sufficiently strong RF signal generating means to power the RFID. Still yet, insulin pen cap 110 may be adapted to have an in situ power generator to replace power source 150. When insulin cap 110 is removed from insulin pen 100, the motion of this removal may be used to generate power for insulin pen 100.

Glucose meter 120 may also include an electronic logbook and a RF transceiver means (similar to RF Tx/Rx unit 130). In one an embodiment, glucose meter 120 may be similar to the commercially available LifeScan One Touch® UltraSmart® Meter. Communication between glucose meter 120 and insulin pen 100 is accomplished via an RF protocol. Glucose meter 120 acts as the "master" and the electronic elements within insulin pen 100 act as a "slave". Glucose meter 120 periodically prompts insulin pen 100 to determine whether an event, e.g., removal of the pen from the case or removal of the cap from the pen, has been recorded. If an event has been recorded by the slave, a message will be sent to glucose meter 120 indicating an event has occurred as—as well as the time of the event. Glucose meter 120 will record the event and may query the patient for further information and supply a notification.

In an embodiment of this invention, a user may remove insulin pen cap 110 from insulin pen 100. In doing so, a RF signal is sent from insulin pen 100 to glucose meter 120 indicating that the user is about to initiate an insulin injection. Glucose meter 120 may then indicate to the user on a LCD screen their most recent pre-prandial and post-prandial glucose level. Glucose meter 120 may prompt the user to insure that these values are correct and if not, glucose meter 120 may allow the user to adjust these values accordingly. In an embodiment of this invention, glucose meter 120 may perform a bolus calculation algorithm where a recommended level of insulin to be injected with insulin pen 100 is shown on the LCD of glucose meter 120. Depending on the situation, the user may inject the recommended insulin dose or inject a different amount. Glucose meter 120 may prompt the user to input the actual dose of insulin allowing for an inventory of insulin remaining in insulin pen 100 to be accessed. When insulin pen 100 is low in insulin (i.e., 10% remaining), glucose meter 120 may prompt the user to procure an additional insulin pen as needed. In another embodiment of this invention, glucose meter 120 may prompt the user to input other types of information after activating event switch 160 such as breakfast, lunch, dinner, snack, alcohol, carbohydrates, fats, calories, proteins, medication, pills, insulin, pump bolus, health notes, ketones, HBA1C, microalbumin, cholesterol, blood pressure, and exercise.

It is an advantage of this invention in that the user does not have to manually record the time at which insulin is injected with insulin pen 100. This simplifies the ability of the user to gather data more effectively to manage their disease. It is a further advantage of this invention in that actuating switch 160 sends a wireless signal to glucose meter 120 prompting the user to perform one several steps that facilitate compliance with the user in regards to their diabetic therapies. Glucose meter 120 may seamlessly display the most recent and relevant glucose concentrations, prompt user for more updated glucose concentrations, recommend an insulin dosage based on recent glucose measurements, or prompt user to input other relevant data.

In an alternative embodiment to this invention, insulin pen 100 may be replaced with a "pill bottle" that contains medication (medication example—Glucotrol XL®). In such an embodiment, the "pill bottle" will include Tx/Rx unit 130, local microcontroller 140, power source 150, and event switch 160. In addition, insulin pen cap 110 must then be replaced with a pill bottle cap.

Also provided by the subject invention are kits for use in practicing the subject methods. The kits may further include software programs recorded on a CD-ROM or the like, which programs may be downloaded to the meter, PDA and/or an external data device for use with the systems. Finally, the kits may further include instructions for using the subject devices and systems. These instructions may be present on one or more of the packaging, label inserts or containers within the kits, or may be provided on a CD-ROM or the like.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A drug delivery system comprising:
   a microprocessor device including a glucose measurement unit;
   a drug delivery device in communication with the microprocessor device, the drug delivery device configured to deliver a drug to a user;
   a holder for the drug delivery device when the device is not in use;
   a detector which detects the removal of the drug delivery device from the holder which causes the microprocessor device to prompt a user to conduct a glucose measurement with the glucose measurement unit, to provide a suggestion for dosage of the drug based on the user's entered input parameters and recommendation from a health care provider previously stored or entered into a memory of the microprocessor device.

2. The system of claim 1, wherein the holder, the detector and the at least one algorithm are incorporated into a case for housing the system.

3. The system of claim 2, wherein the microprocessor device turns on upon removal of the drug delivery device from the holder.

4. The system of claim 1, further comprising means for communicating with a device for storing user information.

5. The system of claim 4, wherein the user information comprises drug dosing information.

6. The system of claim 4, means for communicating comprises wireless communication means.

7. The system of claim 1, wherein the detector is selected from the group consisting of a mechanical switch, a magnetic switch, a density switch, a capacitive switch, an electrical sensor and an optical sensor.

8. The drug delivery system of claim 1, further comprising: a wireless transmitter and receiver to transmit information regarding the user to a remote device.

9. The drug delivery system according to claim 8 wherein the information comprises data on blood glucose measurements of the user and delivery of the drug, which is selected from the group consisting of drug dosage information and timing of drug delivery.

10. An insulin injection system comprising:
a meter adapted for the measurement of glucose concentration in a blood sample, the meter comprising a microprocessor;
an insulin injector;
and a storage case for said insulin injector, the storage case including a detector that activates the meter upon removal of the insulin injector from the storage case, so that the meter prompts a user to conduct a glucose measurement with the meter and provide a suggestion for dosage of the drug based on the user's input parameters and a recommendation from a health care provider previously stored or entered into a memory of the microprocessor device.

11. The system of claim 10, wherein the storage case comprises a storage space to house the meter.

12. The system of claim 10, further comprising wireless communication unit to transmit and receive data to and from an external device.

13. The system of claim 12, wherein the wireless communication unit comprises RF signals.

14. A method of monitoring the use of a drug delivery device, the method comprising:
storing the drug delivery device when the device is not in use;
removing the drug delivery device from storage;
detecting the removal of the drug delivery device from storage;
upon detecting removal of the drug delivery device from storage, prompting a user to conduct a blood glucose measurement with a blood glucose measurement unit;
upon the user conducting a blood glucose measurement, suggesting a dosage of drug to be delivered by the drug delivery device based on the user's input parameter and recommendations from the health care provider previously entered or stored in a memory of a microprocessor; and
requesting that the user enter a dosage actually delivered into the memory of the microprocessor.

15. The method of claim 14, further comprising turning on the blood glucose measurement unit; and requesting that the user perform a glucose measurement.

16. The method of claim 14, further comprising recording the time at which the drug delivery device is removed from storage.

17. The method of claim 14, further comprising transmitting dosage actually delivered to a data storage device.

18. The method of claim 14 further comprising:
transmitting information on blood glucose measurements of the user to a remote device; and
transmitting information on dosage of drugs actually delivered to the remote device.

19. An insulin injection kit comprising:
a system comprising:
a meter adapted for the measurement of glucose concentration in a blood sample, the meter comprising a microprocessor;
an insulin injector; and
a storage case for said insulin injector, the storage case including a detector that activates the meter upon removal of the insulin injector from the storage case, so that the meter prompts a user to conduct a glucose measurement with the meter and provide a suggestion for dosage of the drug based on the user's input parameters and recommendation from a health care provider previously stored or entered into a memory of the microprocessor device;
a plurality of devices selected from the group consisting of lancers, lancets, needles and test strips; and
instructions for using the system.

20. A method of diabetes management for a user, the method comprising:
storing a drug delivery device in a storage case;
upon removal of the drug delivery device from the storage case, prompting a user with a microprocessor device to measure blood glucose value of the user, the microprocessor including a memory having a drug dosage delivery instructions previously stored in the memory from a health care provider based on at least one of a blood glucose value and user's input parameters;
upon the user conducting a measurement of blood glucose value, suggesting a drug dosage based on a measured blood glucose value and the instructions;
querying the user as to whether a dosage of drug was delivered upon removal of the drug delivery device from the storage case; and
verifying with the user of a dosage actually delivered to the user.

21. The method of claim 20, further comprising transmitting data on blood glucose measurements made and drug dosage actually delivered to a remote device.

22. The method of claim 20, further comprising receiving data drug dosage delivery instructions from a remote device.

* * * * *